United States Patent [19]

Rankin

[11] Patent Number: 5,131,412
[45] Date of Patent: Jul. 21, 1992

[54] PEDIATRIC INTRAVENOUS DEVICE

[76] Inventor: Ellen Rankin, 114 Westway Rd., Southport, Conn. 06490

[21] Appl. No.: 749,894

[22] Filed: Aug. 26, 1991

[51] Int. Cl.$^5$ .............................................. A61F 5/37
[52] U.S. Cl. ...................................... 128/877; 128/878; 128/869
[58] Field of Search ............... 128/DIG. 12, DIG. 26, 128/877–882, 157, 165, 156, 862, 845, 89 R

[56] References Cited

U.S. PATENT DOCUMENTS

| | | | |
|---|---|---|---|
| D. 263,423 | 3/1982 | Aslanian | D24/64 |
| 3,590,817 | 7/1971 | Wresch | 128/877 |
| 3,896,799 | 7/1975 | Seeley | 128/87 |
| 3,901,227 | 8/1975 | Klatskin | 128/133 |
| 3,902,484 | 9/1975 | Winters | 128/849 |
| 3,920,012 | 11/1975 | Patel | 128/134 |
| 3,939,829 | 2/1976 | Spann | 128/133 |
| 4,043,330 | 8/1977 | Bansal | 128/133 |
| 4,181,297 | 1/1980 | Nichols | 269/328 |
| 4,204,534 | 5/1980 | Leary | 128/134 |
| 4,265,232 | 5/1981 | Stonich | 128/877 |
| 4,286,588 | 9/1981 | Lovegrove | 128/133 |
| 4,290,425 | 9/1981 | Helfer et al. | 128/133 |
| 4,373,519 | 2/1983 | Errede | 128/156 |
| 4,414,969 | 11/1983 | Heyman | 128/133 |
| 4,422,455 | 12/1983 | Olsen | 128/134 |
| 4,425,913 | 1/1984 | Lewis | 128/133 |
| 4,449,975 | 5/1984 | Perry | 604/179 |
| 4,453,933 | 6/1984 | Speaker | 604/179 |
| 4,470,410 | 9/1984 | Elliot | 128/133 |
| 4,481,942 | 11/1984 | Duncan | 128/133 |
| 4,503,849 | 3/1985 | Morgan et al. | 128/133 |
| 4,612,925 | 9/1986 | Bender | 128/133 |
| 4,615,339 | 10/1986 | Siwek | 128/133 |
| 4,621,808 | 11/1986 | Orchard et al. | 272/119 |
| 4,657,003 | 4/1987 | Wirtz | 128/133 |
| 4,662,366 | 5/1987 | Tari | 128/134 |
| 4,784,653 | 11/1988 | Bolton | 128/156 |
| 4,941,479 | 7/1990 | Russell | 128/877 |

Primary Examiner—Robert A. Hafer
Assistant Examiner—David J. Kenealy
Attorney, Agent, or Firm—Kramer, Brufsky & Cifelli

[57] ABSTRACT

An improved pediatric device for administering intravenous medications and fluids is provided which maintains an infant or toddler's hand, arm, leg or foot in a stationary position to prevent the child from inadvertently dislodging the needle from the vein during sudden movement. The device comprises an anatomically correct age and weight appropriate visco-elastic support molded to conform to the natural contours of the child, said support providing sufficient weight to keep the extremity immobile. The mold is covered with a disposable sleeve-like covering which provides a soft, clean, non-allergenic surface to protect the sensitive skin of an infant or child. The device is affixed to the child with a continuous sleeve of flexible material providing an elongated tubular form for completely securing the limb. The rectangular fabric sleeve has a smooth, moisture absorbing inner surface and is secured by fabric contact engaging means, e.g. Velcro ® fasteners along each edge of the sleeve.

11 Claims, 3 Drawing Sheets

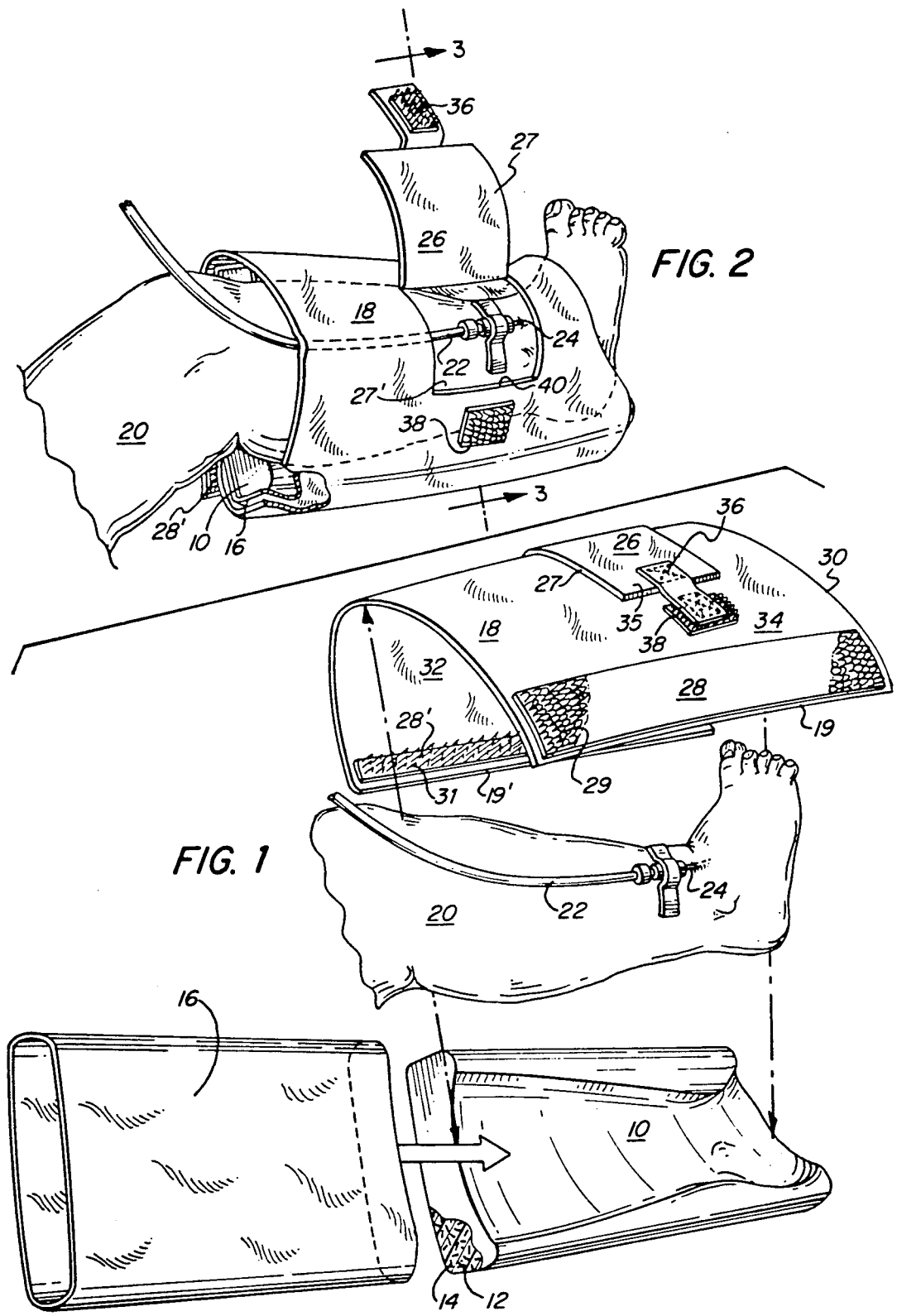

PEDIATRIC INTRAVENOUS DEVICE

BACKGROUND OF THE INVENTION

1. Field of the Invention

This invention relates to medical devices used to secure the extremities, i.e., the hands, arms, legs and feet of an infant or toddler during intravenous (IV) therapy and thus prevent the hazards and complications incurred when the administration of medications and fluids is interrupted due to movement or jarring of the site.

2. Discussion of Prior Art

Maintenance of IV's is a crucial part of hospital work for both doctors and nurses. Currently, the equipment and methods used to restrain an infant or toddler are extremely wasteful in terms of staff time, materials, and equipment. Specifically, because the current devices are not designed to prevent the child from moving the extremity and dislodging the needle from the vein, painful and traumatic repeat insertions are often necessary. To completely understand and appreciate the benefits of the present invention, a discussion of the prior art is presented hereinbelow to demonstrate that despite repeated efforts, the prior art has failed to provide a pediatric intravenous device which has overcome the problems referred to hereinabove.

Aslanian, U.S. Design Pat. No. 263,423 discloses an ornamental design for an anatomically shaped arm support for intravenous feeding. Klatskin, U.S. Pat. No. 3,901,227 and Bansal, U.S. Pat. No. 4,043,330 are both directed to a medical restraining board for medical infusions. None of the foregoing devices address the advantages of a weighted device or the problems inherent in and specific to pediatric patients.

Lewis, U.S. Pat. No. 4,425,913 discloses an anatomically correct molded splint to facilitate the administration of intravenous therapy. This device does not disclose the use of resilient padding which is required to prevent areas of pressure necrosis over bony prominences such as the ankle.

Both Duncan, U.S. Pat. No. 4,481,942 and Siwak, U.S. Pat. No. 4,615,339 describe pediatric arm restraining devices that are used to prevent the infant from using his hands. As both devices wrap around the entire arm, they are useless for IV therapy.

Tari, U.S. Pat. No. 4,622,366 describes an immobilizing arm support specifically designed to facilitate radiographic imaging. Not only is this device specifically designed for adult patients but the patient must remain supine and sedated to maintain the integrity of the IV site.

Wirtz, U.S. Pat. No. 4,657,003 relates to a vacuum device specifically designed to immobilize a fractured limb, head or neck. This device has no use in the administration of IV therapy.

Morgan, et al, U.S. Pat. No. 4,503,849 describes a temporary restraint designed for use when drawing either venous or arterial blood from a patient. That this device was designed to provide a portable method of securing the patient's limb during a brief procedure negates its utility for long term use.

Elliot, U.S. Pat. No. 4,470,410 addresses the problem of interruption of IV therapy due to movement of the patient by designing a protective cover over the site of insertion. However, it does not provide a firm surface or a weighted device to keep the site immobile.

Similarly, both Perry, U.S. Pat. No. 4,449,975 and Speaker, U.S. Pat. No. 4,453,933 attempt to overcome the problem of lost IV catheters due to jarring the needle by the use of adjustable straps. Perry further addresses the complication of skin excoriation caused when adhesive tape is removed by providing an anchor base that acts as "substitute skin." However, both devices fail to recognize that weight and rigidity are essential components in immobilization during IV therapy.

Spann, U.S. Pat. No. 3,939,829; Olsen, U.S. Pat. No. 4,422,455; Heyman, U.S. Pat. No. 4,414,969; and Leary, U.S. Pat. No. 4,204,534 describe restraining devices that attach to the wrist or ankle of a disoriented adult patient to preclude movement. These devices function as cuffs to impede movement and as such do not relate to the administration of intravenous therapy. However, Leary does address the necessity of a limb restraint being constructed of soft pliable material to prevent skin abrasions.

Helfer et al, U.S. Pat. No. 4,290,425, describes a support board with flexible straps used to secure an infant's extremity during IV therapy. There is no recognition in this patent that the extremity cannot be secured against motion without an appropriate weighting agent.

Lovegrove, U.S. Pat. No. 4,286,588 describes a support board with adjustable straps to inhibit the movement of a patient's limb. This device is only designed for adult patients and does not provide for either cushioning or weight.

Nichols, U.S. Pat. No. 4,181,297 describes a clamping device to keep an adult limb immobile for examination purposes. As such, this device is irrelevant for IV therapy.

Patel, U.S. Pat. No. 3,920,012 is directed to a blanket-like material used to wrap an infant's extremities so that examinations involving the face and head may be performed with minimal movement. Again, this invention is irrelevant to IV therapy.

Seeley, U.S. Pat. No. 3,896,799 describes an arm board used in IV therapy. Although this device addresses the aforementioned requirements of rigidity and cushioning, it does not have the necessary weight added to keep the catheter site maintained during an infant or toddler's sudden movement.

SUMMARY OF THE INVENTION

It is an object of the present invention to provide a pediatric intravenous device to secure an infant's or toddler's foot, leg, arm or hand, which can be quickly and easily applied and removed, is low in cost, sanitary, and suitable for use in an emergency context.

Another object of the invention is to provide an intravenous device which is selectively age and weight appropriate for the patient and includes the element of weight which is critical for effective immobilization.

A still further object of the invention is to provide an intravenous unit which is self-contained, requiring no gauze, adhesive tape, and the like for set-up. The use of Velcro ® fasteners to secure the device to the patient avoids the possibility of skin breakdown which also increases the likelihood of infection.

Yet another object of the invention is the provision of a pediatric intravenous device which employs a soft, water-resistant, disposable slip-on-cover which provides a clean, non-irritating surface for contacting the sensitive and tender skin of the infant.

A further object of the invention is to provide comfort to the patient wearing the device even during prolonged periods. Specifically, one advantage of the visco-elastic weighted support of the present invention is that it is soft and will not cause areas of pressure necrosis over bony prominences such as the wrist or ankle after long-term use.

Still another object of the invention is to provide a more visually comforting apparatus for pediatric patients who find viewing a protruding catheter upsetting.

These as well as other objects and advantages are accomplished by the pediatric intravenous device of the present invention which comprises an anatomically correct support molded from visco-elastic material. This material is soft, but firm and has the property of being able to deform under slight pressure and resume its original shape when the pressure is removed. It is made from a highly plasticized resin with a weighting agent added. Consequently, the device can be readily increased in weight with the advancing age of the child. The device of the present invention integrates the functions of weight, stabilization, and resilient padding in one unit. The support is anatomically correct and age specific. The visco-elastic material contains a weighting agent uniformly dispersed therein to impart weight to the device which can vary from one to ten pounds. Each support is designed to fit the arm or leg of an infant or toddler between one month and five years of age. Preferably, three different supports are kept available. One is designed to fit under the foot with a half moon pocket for the child's heel. A second is made to be attached above the forearm with a small indentation for the elbow. A third is designed to fit under the forearm and contain small grooves for the fingers. Based on growth charts, these supports can be varied in size to be suitable for children one month, two months, three months, six months, nine months, one year, two years, three years, four years and five years of age.

The support is covered with a soft, disposable hydrophobic slip-on cover or stockinette. The ability to dispose of each stockinette covering after patient use precludes the possibility of contamination between patients with infectious blood or blood products. The stockinette covering can be color-coded by age group to facilitate immediate preparedness in an emergency.

The covered support is secured by a protective retaining device comprising an elongated sleeve which provides protective padding for the intervention site and minimizes movement and dislodgement. The protective retaining sleeve can be joined with Velcro® fasteners instead of adhesive tape.

DESCRIPTION OF THE DRAWINGS

The present invention will become more apparent upon reference to the appended drawings wherein:

FIG. 1 is an exploded view of the device of the present invention enabling ready identification of the component parts of the device;

FIG. 2 is an isometric view of the device of the present invention as employed in conjunction with the leg and foot of a pediatric patient;

DETAILED DESCRIPTION

Figure 3:
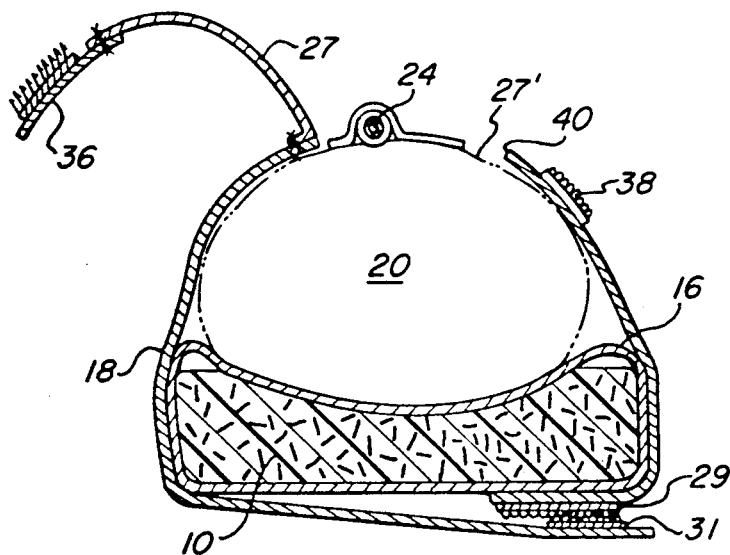
FIG. 3 is a sectional view taken along line 3—3 in FIG. 2.

Referring now to FIG. 1, the present invention comprises a visco-elastic support 10 molded to anatomically correspond to a portion of the leg, foot, arm or hand of a pediatric patient. Generally, the support ranges from about 1 to 3 inches in width and from about 3 to 6 inches in length. The support 10 is made of a visco-elastic material 12 with a particulate weight-adding agent 14 substantially homogeneously dispersed within the visco-elastic material. In general, the term "visco-elastic" refers to the soft, compressible elastic materials which are able to deform under slight pressure and resume their original shape when the pressure is removed. In particular, the preferred visco-elastic material described herein can be characterized as either a highly plasticized resin or a plasticizing material thickened with a minor portion of resin.

The following is a detailed description of the components used in making the weighted visco-elastic material employed in the present invention.

Generally, the weighted visco-elastic material used in the present invention comprises, by weight, 77-97% plasticizer and 3-15% resin, with optional use of up to 2% thixotropic thickening agent, up to 2% stabilizer, up to 2% stabilizer enhancer and up to 2% surfactant. All of the foregoing are used to make a visco-elastic material to which is added a particulate weight-adding agent, in a weight ratio of from 1:10 to 2:1 weight-adding agent to visco-elastic material.

The plasticizer employed in the present invention is preferably a dialkyl phthalate such as, for example, diundecylphthalate, diisononylphthalate, and the like.

The resin employed in the present invention is preferably a polyvinyl chloride resin. In addition to polyvinyl chloride resins, other visco-elastic materials such as silicones and urethanes can similarly be employed. The resin and plasticizers used must be compatible.

The preferred thixotropic thickening agent is silicon dioxide also known as fumed silica. Other thixotropic thickening agents can be employed such as clay materials with quaternary ammonia or organic thixotropic agents such as castor oil derivatives or ethylene complexes.

The stabilizers employed in the present invention allow the resin and plasticizer composition to be processed at elevated temperatures without degradation. Typically, the stabilizers are barium zinc, calcium zinc, and zinc tin stabilizers. Most preferred is a barium zinc phenate stabilizer.

Stabilizer enhancers can be used to increase the effectiveness of the stabilizer or, if desired, additional stabilizers can be used instead of the stabilizer enhancer. Suitable stabilizer enhancers for the present invention are epoxidized soybean oils or other epoxidized soy-oil products.

The preferred surfactant is Kelecin F, available from Spencer Kellog Division of Textron Incorporated, Buffalo, N.Y. Other surfactants that can be used include Surfysol 104A.

The particulate weight adding agent 14 can be barium sulfate, lead oxide, iron oxide as well as other minerals with a specific gravity of at least 4. Barium sulfate is preferred because it is inexpensive and is less abrasive on processing equipment than other metal oxides. The particulate weight adding agent is preferably ground to a powder such that substantially all, about 97%, passes through a 200 mesh screen. OSHA regulations may restrict the use of oxides of certain metals, e.g., lead, for this application.

Figure 4:
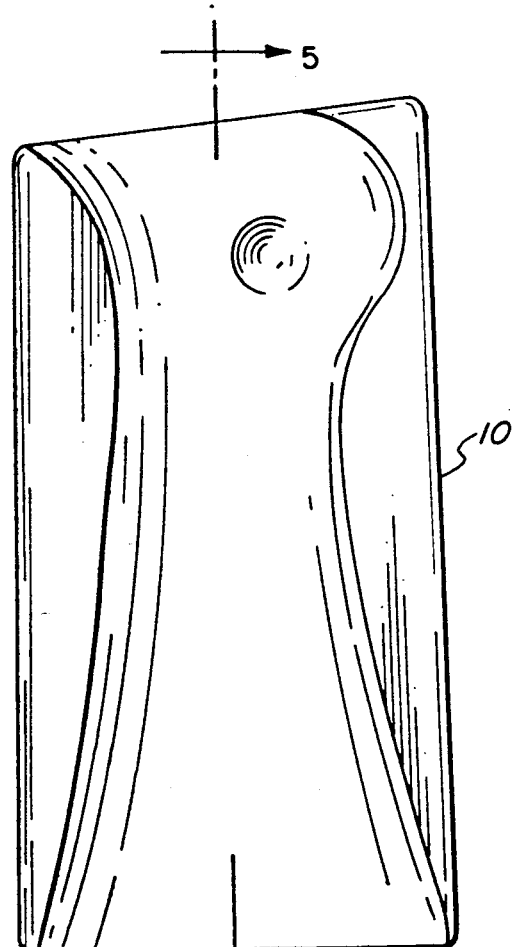
FIG. 4 is a plan view of the weighted substrate as anatomically molded to conform to the leg and heel of a pediatric patient.
Figure 5:
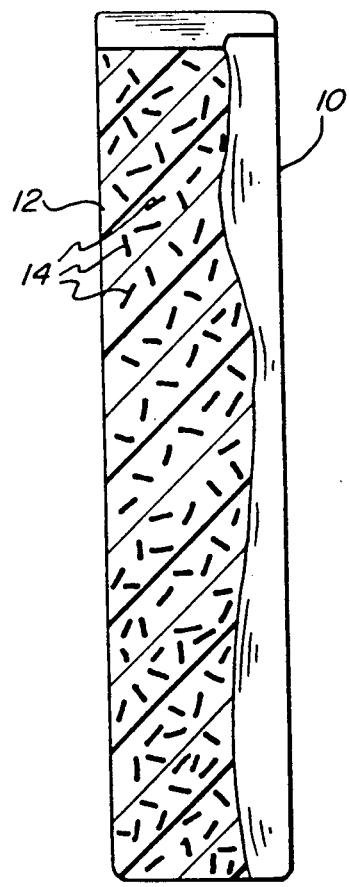
FIG. 5 is a sectional view taken along line 5—5 in FIG. 4.
Figure 6:
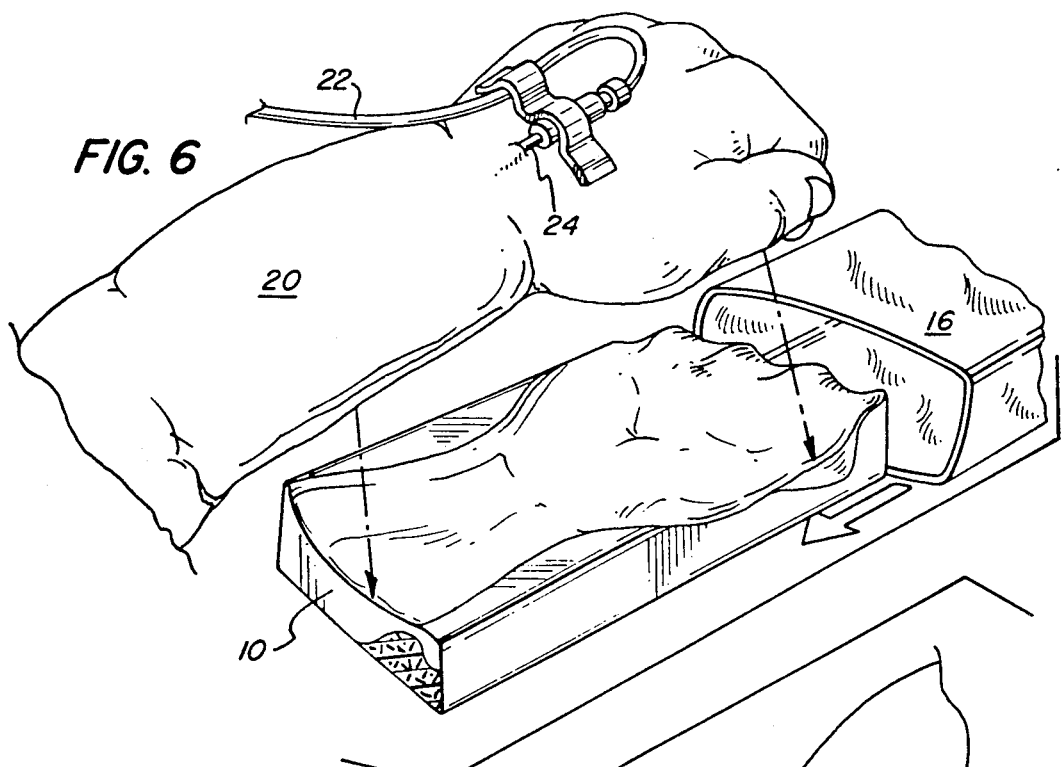
FIG. 6 is a partially exploded view illustrating the manner in which the device of the present invention is employed when the arm and hand of a pediatric patient is placed on the support palm down.
Figure 7:
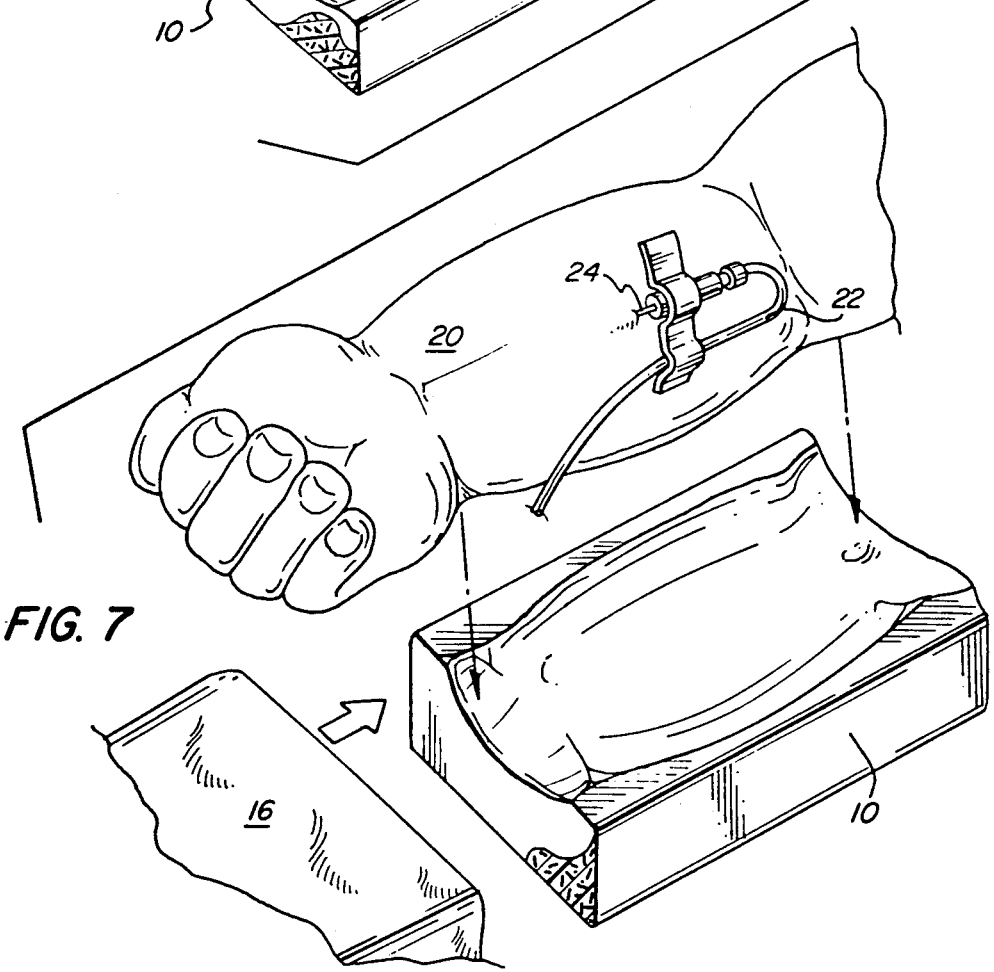
FIG. 7 is a partially exploded view illustrating the manner in which the device of the present invention is employed when the arm and hand of a pediatric patent is placed on the support palm up.

The method for producing the weighted visco-elastic material includes the steps of mixing the plasticizer and the resin to form a plasticizer-resin mixture, substantially homogeneously mixing from about 1 to 20 parts by weight of a particulate weight-adding agent to one part by weight of the plasticizer-resin mixture, heating the resulting mixture to the fusion temperature before or after addition of the weight adding agent and thereafter, cooling the resulting weighted plasticizer-resin mixture to form the weighted visco-elastic material. The fusion temperature is that temperature at which the resin and the plasticizer form a homogeneous system. Typically the fusion temperature for the preferred phthalate-PVC resin system ranges between about 325° and 375° F. The resulting visco-elastic mixture can then be poured into an appropriate mold and allowed to cool. The visco-elastic support 10 thereby obtained is an anatomically correct molded shape (see, for example, FIGS. 4, 6 and 7) suitable for use in conjunction with the immobilization of the extremities of pediatric patients.

In a preferred embodiment, the present invention comprises a weighted visco-elastic substrate 10 of anatomically correct shape, i.e., corresponding to the shape of a portion of an extremity, e.g., a leg, foot, arm or hand of a pediatric patient. Generally, the substrate is approximately one to three inches in width and three to six inches in length.

The weighted visco-elastic substrate 10 is envelope within
d a disposable paper or polymeric non-woven sleeve-like covering 16 which provides a soft, clean non-allergenic surface for contacting the skin so that the skin does not come into direct contact with the visco-elastic material. The materials from which the outer cover is constructed are commercially available. The sleeve 16 can comprise paper coated or impregnated with a hydrophobic material such as a polyolefin or vinyl polymer or thermally bonded fibers spun from a polymeric material, preferably from a polyolefin. Additionally, if desired, the sleeve can contain a foamed material such as a polyurethane, polystyrene, poly (vinyl chloride) foam, and the like. The materials forming the sleeve-like covering are preferably hydrophobic and sufficiently porous so as to pass air and moisture from a patient's skin. Since the cover is porous, heat and moisture generated between the patient's skin and the adjacent surfaces of the substrate are dissipated through the porous outer cover. Typical of such substrate covers 16 is the "Armboard Sleeve", Catalog No. NUN24296, available from Medline Industries, Inc., Mundelein, Ill. 60060, which comprises a non-woven fabric made from fiberboard (compressed wood fibers), polyurethane foam and poly (vinyl chloride).

The device is held in place by a continuous protective sleeve 18 of resilient material, preferably relatively elastic and stretchable, providing an elongated tubular form for completely encompassing a limb 20. Specifically, the resilient sleeve 18 can contract in position for firmly retaining the tubing 22 connected with the insertion means 24, thereby minimizing disturbances of the intervention site and dislodgement.

Further, the retaining sleeve 18 has a portal opening 26 adapted to be located over and permit access to the site of insertion to allow inspection of the site for phlebitis and other untoward effects. The portal opening 26 can either be formed by being cut out of the protective sleeve 18 to form a flap 27 and a commensurate aperture or opening 27' in the sleeve 18 or the opening 27' can be cut out of sleeve 18 and an appropriate flap 27 sewn or otherwise adhered to the sleeve. A retaining tab 36, preferably of Velcro ® material is secured to the free lateral edge 35 of the flap 27 and can be detachably secured to the protective sleeve 18 with a securing patch 38 which is positioned on the sleeve 18 proximate to the edge 40 of the opening 27' for retaining the flap 27 in its closed position. The securing patch 38 is also preferably made of Velcro ® material.

Typically, the site of insertion is a vein in the arm, hand, leg or foot of the patient. The difficulty most health care practitioners have in accessing veins in the infant and toddler population is simply due to the physical characteristics of their circulatory system and the large amount of subcutaneous fat found on each extremity. Specifically, children have notably poor peripheral veins. Not only are the superficial veins extremely small but they are fragile as well. Constrained by these circumstances, maintenance of IV site becomes even more crucial.

The veins most commonly used are found on the arm and the foot. With the child's palm facing up (see FIG. 7), the most accessible superficial veins on the arm are the cephalic and accessory cephalic veins; the basilic vein; the median cubital vein; and the anterior ulnar vein. With the child's palm facing down (see FIG. 6), the most accessible superficial veins are found in the dorsal venous network. The dorsal venous arch consists of the three superficial veins on the dorsum of the hand that form the cephalic vein that is found near the wrist. On the foot (see FIG. 1), the superficial veins consist of the great and small saphenous veins and their tributaries, the dorsal venous arch which is comprised of the dorsal digital veins, the intercapitular veins and the common digital veins found on the dorsum of the foot.

The sleeve 18 is made of moisture absorbent material which permits air circulation and is made in sizes specific to the infant and toddler population. The tension and firmness with which the sleeve is secured around the limb ca be readily adjusted by the
n degree to which the resilient material is stretched.

The material readily conforms to the infant or toddler's arm or leg to snugly follow the body contour. The protective sleeve 18 is applied by first positioning one of its longitudinal edges 19 or 19' to extend in the direction between, for example, the knee and ankle of the patient and displaced from the intervention site. With said longitudinal edge held in this position, the remaining portion of the sleeve is wrapped around the leg so that the portal opening 26 is positioned over the desired intervention site. In this manner, when the protective device is worn by the patient, the intervention site is completely enclosed and not visible, thereby providing an agitated child with a more acceptable and less frightening appearance. Thus, the site is protected against dislodgement when the child is thrashing or engaging in other random movement. The sleeve 18 can be readily applied and removed when required with no danger of tissue trauma or discomfort during the removal of adhesive tape.

The protective sleeve 18 is formed in a flat, generally rectangular shape constructed of a soft padded or quilted pliable cloth fabric of knitted or woven construction. The fabric covering provides a soft, clean, washable, non-allergenic surface for contacting the delicate skin of an infant or toddler. The fabric can be formed from yarn containing hydrophilic fibers, such as cotton, so as to be readily absorbent and to assist in keeping any moisture away from the skin of an infant to prevent irritation. The fabric covering comprises a single piece of fabric which is folded over one of the edges and held together with self-fastening strips 28 and 28'. Thus, the materials are strong, durable and moisture-absorbent to permit air circulation. This material is also relatively inexpensive to manufacture and simple to construct. Finally, it is easy to apply and remove.

Preferably, the protective sleeve 18 comprises a rectangular sheet 30 having an inner sheet 32 of soft cloth material of substantial length so as to make one complete lap around a limb, and an outer sheet 34 of any suitable soft cloth material made with a short close pile such as a velveteen fabric. The inner sheet 32 can comprise an inner layer of soft fabric which engages and contacts the patient to prevent injury thereto, and an outer layer of soft cloth material attached to the back of said inner layer. Any suitable means can be employed for attaching the two cloth layers, but it is preferred that they be sewn along the unturned edges. The sleeve 18 can be made in sizes specific to the infant and toddler population.

Finally, each longitudinal edge of the sleeve is bound with a Velcro ® strip 28 and 28' which is relatively wide to allow attachment with a degree of variation in circumference of the sleeve. The term "Velcro ®" as used herein is a trademark widely associated with "hook and pile" fibrous fastener elements. One of the attaching strips 28 contains the "pile" 29 in relatively stiff fibers resembling a carpet. The other strip 28' includes the "hook" elements 31 comprising a large plurality of hook-shaped fibers. These strips mate together firmly but not inseparably upon being pressed together. Disengagement is effected by a hand "peeling" force. U.S. Pat. No. 4,047,250 is a specific reference identifying and defining Velcro ®, the relevant portions of which are incorporated herein by reference.

The pediatric intravenous device of the present invention provides a comfortable device for intravenous feeding and the like which is inexpensive to manufacture, sanitary, and suitable for a wide variety of uses for hospitalized pediatric patients.

Although various preferred embodiments of the present invention have been disclosed herein for illustrative purposes, it will be appreciated by those skilled in the art that many additions, modifications and substitutions are possible without departing from the scope and spirit of the invention as defined in the accompanying claims.

What is claimed is:

1. A pediatric intravenous device comprising a molded visco-elastic substrate containing a particulate weight-adding agent substantially homogeneously dispersed therein, which substrate substantially conforms to the shape and contour of an extremity, a disposable sleeve substantially enveloping said substrate, and a resilient retaining sleeve adapted to encircle said substrate and a portion of an extremity to which an intravenous infusion is being administered, said device substantially immobilizing said extremity during said infusion.

2. A pediatric intravenous device as defined in claim 1 wherein the disposable sleeve comprises a hydrophobic non-woven fabric which is sufficiently porous to permit dissipation of heat and moisture generated between the extremity and the substrate.

3. A pediatric intravenous device as defined in claim 2 wherein said sleeve comprises hydrophobically treated paper.

4. A pediatric intravenous device as defined in claim 2 wherein said sleeve comprises thermally bonded polymeric fibers.

5. A pediatric intravenous device as defined in claim 1 wherein the retaining sleeve contains a portal opening adapted to permit inspection of the intravenous insertion site.

6. A pediatric intravenous device as defined in claim 5 wherein a flap in or on the retaining sleeve cooperates with an aperture in said sleeve to form said portal opening.

7. A pediatric intravenous device as defined in claim 6 wherein the flap contains a retaining tab secured to the free lateral edge thereof which is adapted to be detachably secured to the retaining sleeve by cooperation with a securing patch on said sleeve.

8. A pediatric intravenous device as defined in claim 7 wherein the retaining tab and the securing patch comprises Velcro ® material.

9. A pediatric intravenous device as defined in claim 5 wherein the retaining sleeve comprises a hydrophilic material.

10. A pediatric intravenous device as defined in claim 9 wherein the retaining sleeve exhibits elasticity, is flat and rectangular in shape, and is adapted to be rolled about the substrate and the extremity to form a sleeve.

11. A pediatric intravenous device as defined in claim 10 wherein Velcro ® strips are attached along the laterally extending edges of the rectangular retaining sleeve to effect closure of the sleeve and permit variation in the circumference thereof.

* * * * *